United States Patent
Ehman et al.

(10) Patent No.: US 8,615,285 B2
(45) Date of Patent: Dec. 24, 2013

(54) PASSIVE ACOUSTIC DRIVER FOR MAGNETIC RESONANCE ELASTOGRAPHY

(75) Inventors: Richard L Ehman, Rochester, MN (US); Phillip J. Rossman, Rochester, MN (US); Jun Chen, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 919 days.

(21) Appl. No.: 12/418,204

(22) Filed: Apr. 3, 2009

(65) Prior Publication Data

US 2009/0299168 A1 Dec. 3, 2009

Related U.S. Application Data

(60) Provisional application No. 61/042,437, filed on Apr. 4, 2008, provisional application No. 61/080,420, filed on Jul. 14, 2008.

(51) Int. Cl.
*A61B 5/05* (2006.01)
(52) U.S. Cl.
USPC .............. 600/411; 600/407; 324/309; 606/32
(58) Field of Classification Search
USPC ................... 600/407, 421, 437, 442; 324/315; 381/59, 63–64, 423
See application file for complete search history.

(56) References Cited

U.S. PATENT DOCUMENTS

| | | | |
|---|---|---|---|
| 4,864,610 A * | 9/1989 | Stevens .......................... | 379/431 |
| 5,010,878 A * | 4/1991 | Kline et al. ..................... | 601/27 |
| 5,606,971 A | 3/1997 | Sarvazyan | |
| 5,810,731 A | 9/1998 | Sarvazyan et al. | |
| 5,952,828 A | 9/1999 | Rossman et al. | |
| 5,977,770 A | 11/1999 | Ehman | |
| 6,037,774 A * | 3/2000 | Felmlee et al. ................ | 324/318 |
| 6,486,669 B1 | 11/2002 | Sinkus et al. | |
| 6,862,468 B2 * | 3/2005 | Smith ........................... | 600/410 |
| 7,002,347 B2 * | 2/2006 | Feiweier et al. .............. | 324/318 |
| 7,034,534 B2 * | 4/2006 | Ehman et al. .................. | 324/318 |
| 7,068,867 B2 * | 6/2006 | Adoram et al. ................. | 385/12 |
| 7,278,963 B2 * | 10/2007 | Schneider et al. ............. | 600/25 |
| 7,307,423 B2 | 12/2007 | Ehman et al. | |
| 2003/0149359 A1 * | 8/2003 | Smith ........................... | 600/437 |
| 2003/0210811 A1 * | 11/2003 | Dubowsky et al. ............ | 382/128 |
| 2005/0018868 A1 * | 1/2005 | Chick et al. .................... | 381/349 |
| 2005/0157900 A1 * | 7/2005 | Litovsky et al. ............... | 381/349 |
| 2005/0196012 A1 * | 9/2005 | Babb et al. ..................... | 381/412 |
| 2006/0012367 A1 * | 1/2006 | Meaney et al. ................ | 324/315 |
| 2006/0029525 A1 * | 2/2006 | Laugharn et al. .............. | 422/130 |
| 2006/0094988 A1 * | 5/2006 | Tosaya et al. .................. | 601/2 |
| 2006/0189868 A1 * | 8/2006 | Gleich et al. .................. | 600/437 |
| 2006/0241432 A1 * | 10/2006 | Herline et al. ................. | 600/437 |
| 2007/0099531 A1 * | 5/2007 | Efremova et al. ............. | 442/370 |
| 2007/0156156 A1 * | 7/2007 | Badie .............................. | 606/129 |

OTHER PUBLICATIONS

Bensamoun et al, Determination of Thigh Muscle Stiffness Using Magnetic Resonance Elastography, Journal of Magnetic Resonance Imaging, 23:242-247 (2006).

* cited by examiner

*Primary Examiner* — James Kish
*Assistant Examiner* — Michael N Fisher
(74) *Attorney, Agent, or Firm* — Quarles & Brady, LLP

(57) ABSTRACT

An acoustic driver system for use in applying an oscillating stress to a subject undergoing a magnetic resonance elastography (MRE) examination includes a flexible passive driver located in the bore of the magnet and in contact with the subject. A remotely located active driver is acoustically coupled to the passive driver and produces acoustic energy in response to an applied current. The passive driver produces shear waves in response to the acoustic energy and are directed into the body of the subject undergoing the MRE examination.

9 Claims, 8 Drawing Sheets

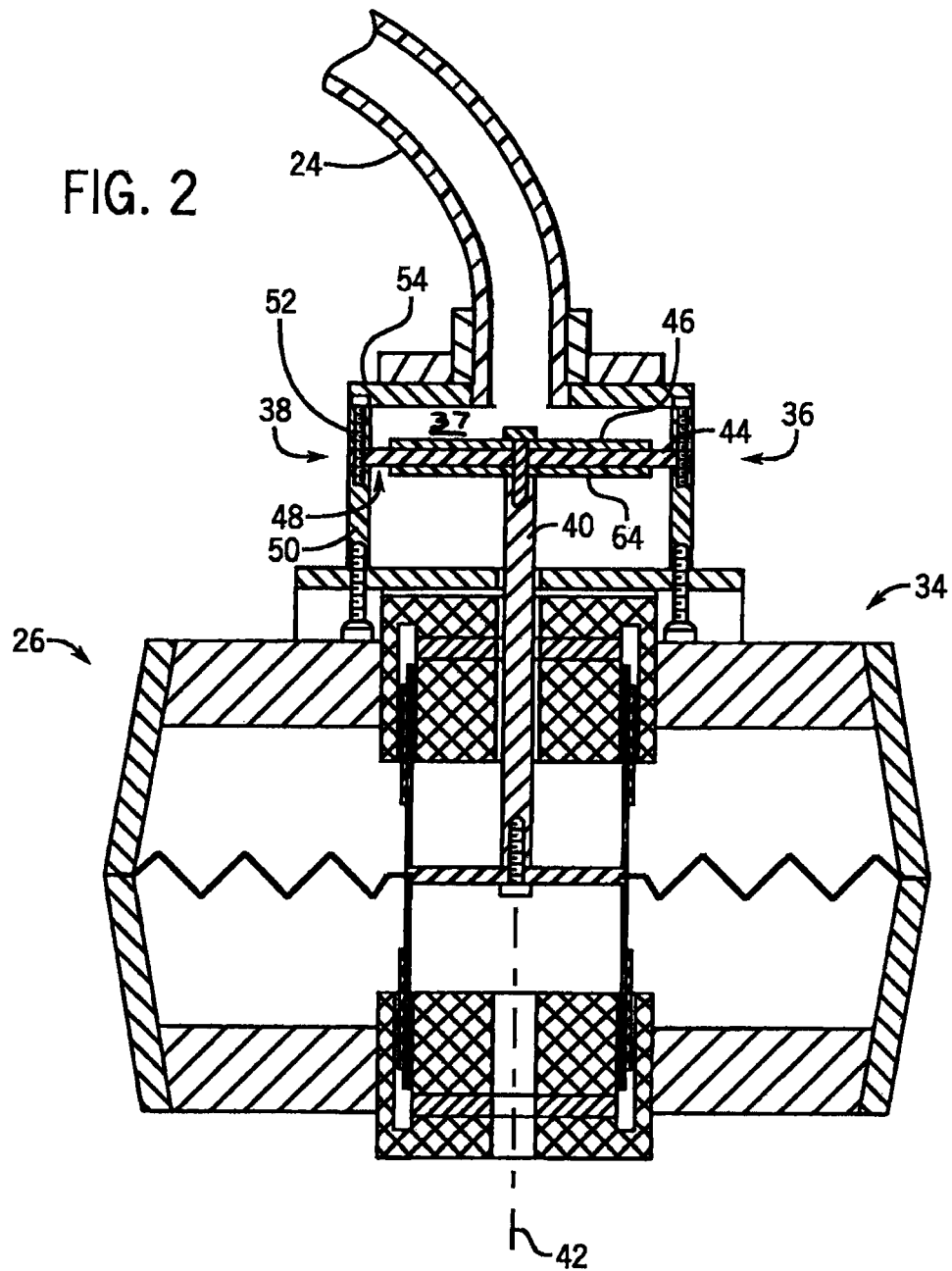

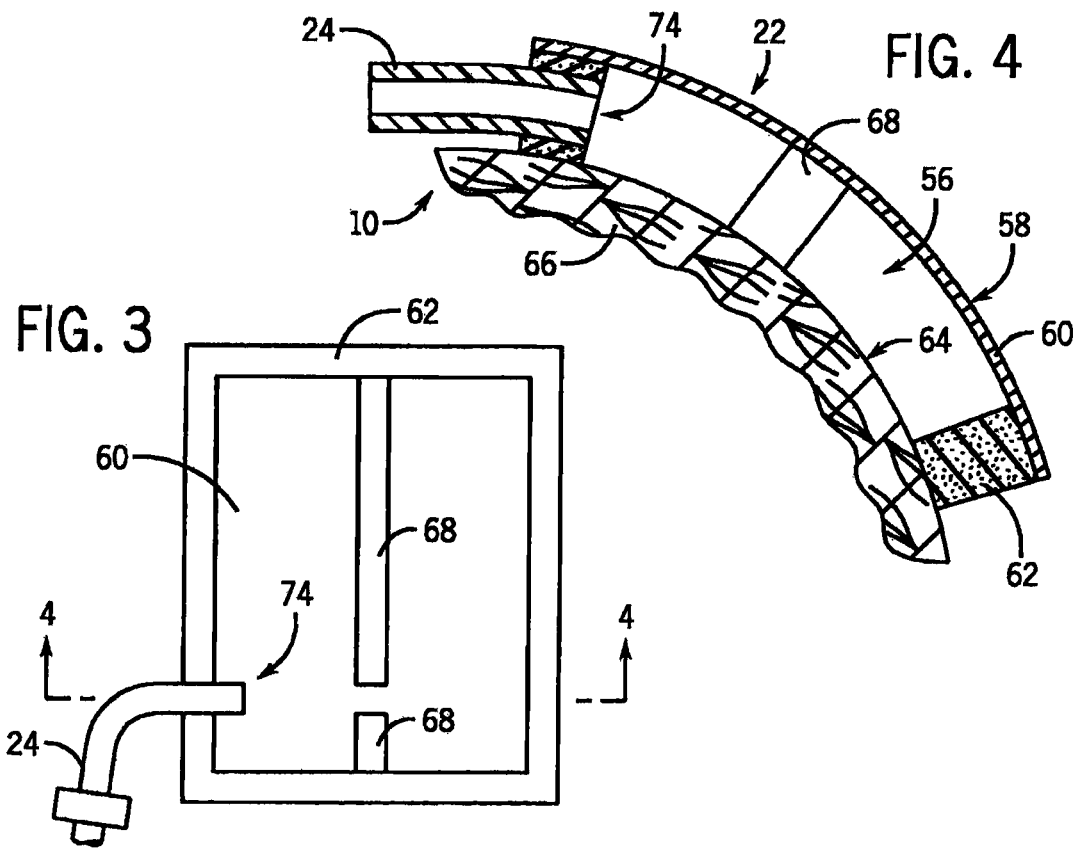
FIG. 4
FIG. 3
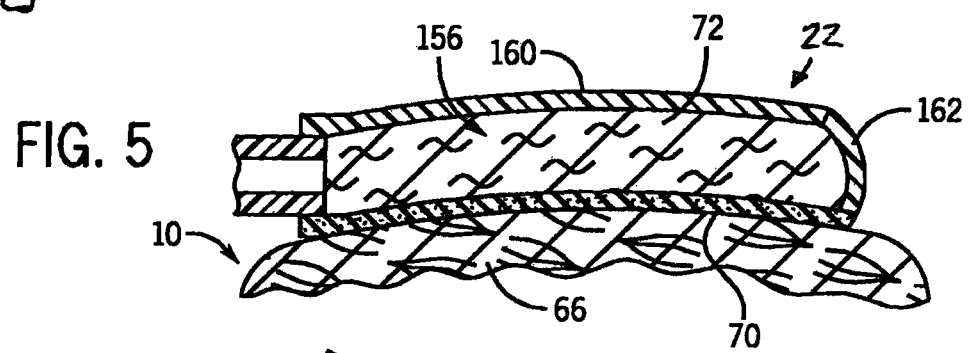
FIG. 5
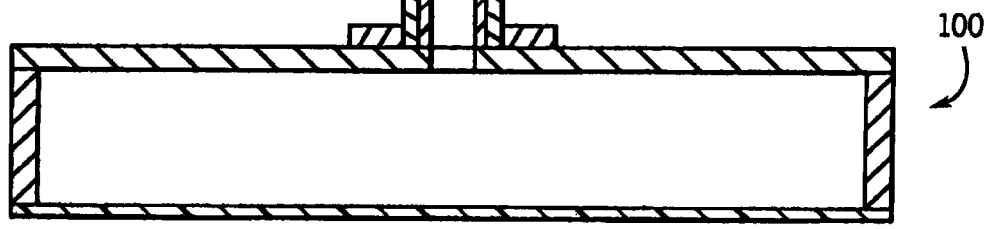
FIG. 6
PRIOR ART

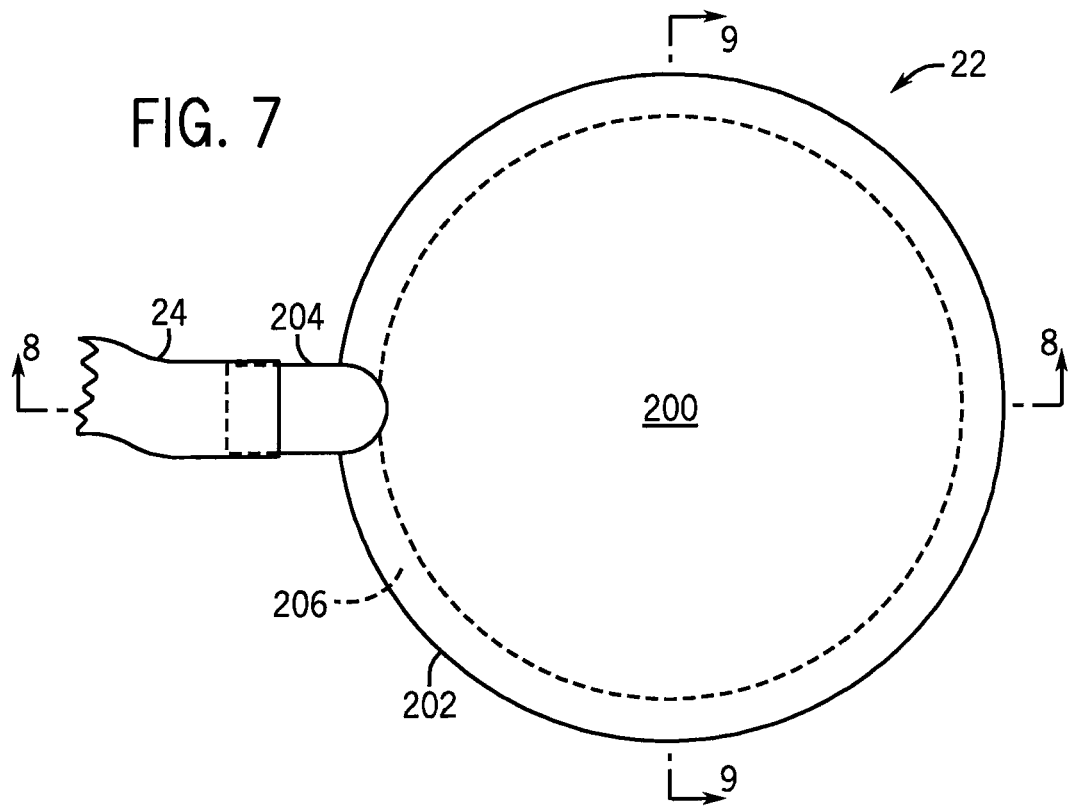
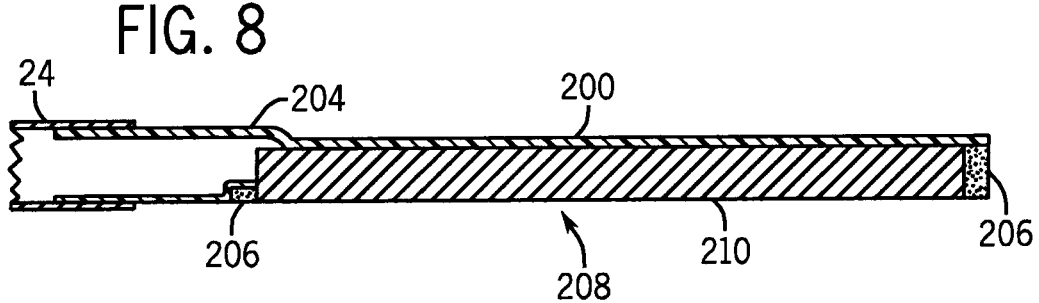
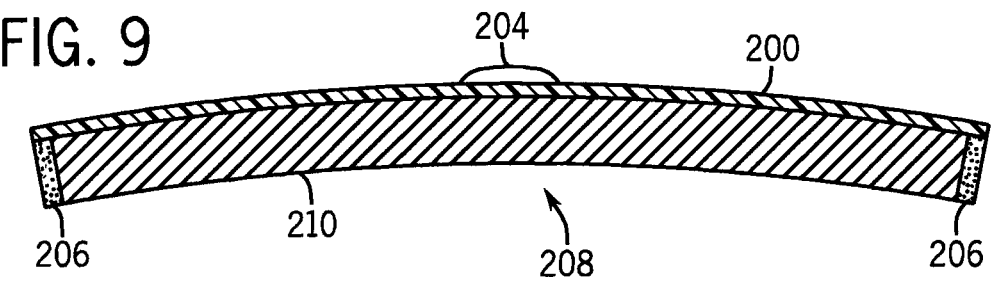

PASSIVE ACOUSTIC DRIVER FOR MAGNETIC RESONANCE ELASTOGRAPHY

CROSS-REFERENCE TO RELATED APPLICATIONS

This application is based on, claims the benefit of, and incorporates by reference U.S. Provisional Application Ser. No. 61/042,437 filed Apr. 4, 2008, and entitled "SYSTEM AND METHOD FOR MAGNETIC RESONANCE ELASTORGRAPHY" and U.S. Provisional Application Ser. No. 61/080,420 filed Jul. 14, 2008, and entitled "PASSIVE ACOUSTIC DRIVER FOR MAGNETIC RESONANCE ELASTOGRAPHY."

STATEMENT REGARDING FEDERALLY SPONSORED RESEARCH

This invention was made with government support under Grant No. EB001981 awarded by the National Institutes of Health. The United States Government has certain rights in this invention.

BACKGROUND OF THE INVENTION

The field of the invention is nuclear magnetic resonance imaging methods and systems. More particularly, the invention relates to devices for implementing magnetic resonance elastography (MRE).

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging (MRI) systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient, a physician can feel differences in the compliance of tissues and detect the presence of tumors and other tissue abnormalities. Unfortunately, this valuable diagnostic tool is limited to those tissues and organs which the physician can feel, and many diseased internal organs go undiagnosed unless the disease happens to be detectable by one of the above imaging modalities. Tumors (e.g., of the liver) that are undetected by existing imaging modalities and cannot be reached for palpation through the patient's skin and musculature, are often detected by surgeons by direct palpation of the exposed organs at the time of surgery. Palpation is the most common means of detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

It has been found that MR imaging can be enhanced when an oscillating stress is applied to the object being imaged in a method called MR elastography (MRE). The method requires that the oscillating stress produce shear waves that propagate through the organ, or tissues to be imaged. These shear waves alter the phase of the MR signals, and from this the mechanical properties of the subject can be determined. In many applications, the production of shear waves in the tissues is merely a matter of physically vibrating the surface of the subject with an electromechanical device such as that disclosed in U.S. Pat. No. 5,592,085. For example, shear waves may be produced in the breast and prostate by direct contact with the oscillatory device. Also, with organs like the liver, the oscillatory force can be directly applied by means of an applicator that is inserted into the organ.

A number of driver devices have been developed to produce the oscillatory force needed to practice MRE. As disclosed in U.S. Pat. Nos. 5,977,770, 5,952,828, 6,037,774, and 6,486,669, these typically include a coil of wire through which an alternating current flows. This coil is oriented in the polarizing field of the MRI system such that it interacts with the polarizing field to produce an oscillating force. This force may be conveyed to the subject being imaged by any number of different mechanical arrangements. Such MRE drivers can produce large forces over large displacement, but they are constrained by the need to keep the coil properly aligned with respect to the polarizing magnetic field. In addition, the current flowing in the driver coil produces a magnetic field which can alter the magnetic fields during the magnetic resonance pulse sequence resulting in undesirable image artifacts.

Another approach is to employ piezoelectric drivers as disclosed in U.S. Pat. Nos. 5,606,971 and 5,810,731. Such drivers do not produce troublesome disturbances in the scanner magnetic fields when operated, but they are limited in the forces they can produce, particularly at larger displacements. Piezoelectric drivers can also be oriented in any direction since they are not dependent on the polarizing magnetic field direction for proper operation.

Yet another approach is to employ an acoustic driver system as described in U.S. Pat. Nos. 7,034,534 and 7,307,423. The acoustic driver system includes an active driver located remotely from the MRI system and acoustically coupled by a tube to one or more passive drivers positioned on the subject being imaged. The passive drivers do not disturb the magnetic fields and may be oriented in any direction.

There are clinical situations where existing passive drivers cannot reliably or comfortably be positioned to adequately vibrate, or illuminate, tissues in the region of interest. Existing MRE passive drivers, such as the prior art driver 100 shown in FIG. 6, are rigid and cylindrical and consequently do not always conform well to the anatomical shape of a subject. As a result, incomplete surface area contact between the subject and the passive driver causes reduced MRE driver efficiency and a reduced MRE signal. These problems are most problematic in, but not limited to, situations where the mass loading of the region of interest is high or where there is a need to vibrate tissue deeper within the body.

SUMMARY OF THE INVENTION

The present invention is a passive acoustic driver that receives acoustic pressure waves through a tube and imparts pressure waves to a subject of an imaging procedure. In one implementation, the passive driver includes a plate that forms the back wall of an acoustic cavity, an intake pipe which is connectable to the tube and conveys acoustic pressure waves into the acoustic cavity, and a wall extending from the rim of the plate to define the perimeter of the acoustic cavity and to engage the subject of the examination. The wall includes a flexible material that engages the subject and conforms to the shape of the subject.

In another implementation, the present invention is an acoustic driver system for producing a stress on a subject undergoing an imaging procedure. The system includes an active driver located remotely from the subject that includes a diaphragm operable to produce oscillating acoustic energy by actuating the diaphragm. They system includes a passive driver positioned on a surface of the subject. The passive driver has a flexible enclosure which defines an enclosed chamber when placed on the subject. The flexible enclosure has a port for receiving acoustic energy. The active driver is acoustically coupled to the passive driver such that the surface of the subject upon which the flexible enclosure rests vibrates in response to the acoustic energy produced by the active driver.

One aspect of the invention is to improve the patient comfort when using a passive acoustic driver. The driver may flex to follow the general contour of the subject being imaged. The driver compresses as needed to uniformly distribute the force holding the passive driver in place. Pressure points are thus avoided.

Another aspect of the invention is to provide a passive acoustic driver that does not require an integral flexible membrane. Instead, the engagement of the wall with the subject seals off the acoustic cavity from the surroundings such that the subject's skin within the encircled area acts as a flexible membrane to convey acoustic pressure waves to the tissues there beneath.

Another aspect of the invention is to provide a passive acoustic driver with a disposable element that can be changed between subjects. The wall may include a flexible foam ring that may be easily removed for cleaning or disposal.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2 is a cross-sectional view of an active driver used in the MRI system of FIG. 1;

FIG. 3 is a bottom plan view of one implementation of the passive driver which forms part of the MRI system of FIG. 1;

FIG. 4 is a cross-sectional view of the passive driver of FIG. 3 taken along line 4-4 showing the driver on a subject and slightly flexed;

FIG. 5 is a cross-sectional view of an alternative implementation of the passive driver which forms part of the system of FIG. 1;

FIG. 6 is a cross-sectional view of a prior art passive driver;

FIG. 7 is a top plan view of a second implementation of the passive driver which forms part of the system of FIG. 1;

FIG. 8 is a cross-sectional view of the passive driver of FIG. 7 taken along line 8-8;

FIG. 9 is a cross-sectional view of the passive driver of FIG. 7 taken along line 9-9 showing the driver slightly flexed;

DETAILED DESCRIPTION OF THE PREFERRED EMBODIMENT

Figure 1:
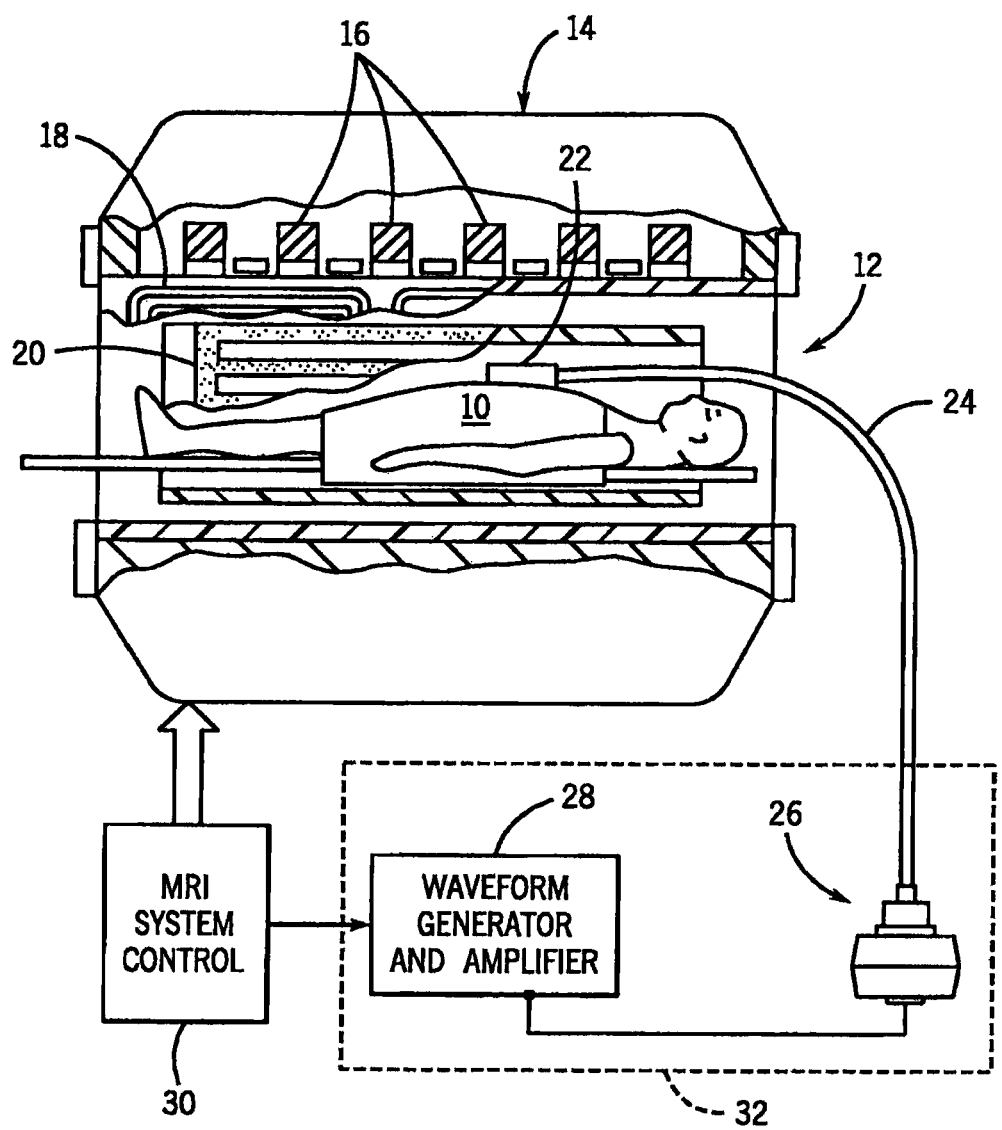
FIG. 1 is a pictorial representation of an MRI system which employs an implementation of the present invention.

The present invention is employed in a system such as that described in the previously-cited U.S. Pat. No. 5,592,085 which provides a means for measuring the strain in gyromagnetic materials, such as tissues, using MR methods and apparatus. The present invention may also be employed with other medical imaging modalities including, but not limited to, ultrasound. Referring to FIG. 1, a subject to be examined 10 is placed in the bore 12 of an MRI system magnet 14 and is subjected to magnetic fields produced by a polarizing coil 16, gradient coils 18 and an RF coil 20 during the acquisition of MR data from a region of interest in the subject 10. The homogeneity of these magnetic fields is important and any objects placed in the bore 12 must be carefully constructed of materials that will not perturb them.

The present invention is a passive driver system that may be placed on the subject 10 and energized to produce an oscillating, or vibratory, stress. It includes a passive driver 22 positioned over the region of interest in the subject 10 and connected by means of a tube 24 to a remotely located active acoustic driver 26. The active driver 26 is remote from the bore 12 of the magnet 14 in the sense that it is positioned away from the strong magnetic fields produced by the magnet 14 where its operation is not impeded by those fields, and where its operation will not perturb the MRI system magnetic fields. The active driver 26 is electrically driven by a waveform generator and amplifier 28, which in turn is controlled by a pulse sequencer in the MRI system control 30. The MRI system control 30 directs the MRI system to perform an MRE scan by driving the RF coil 20 and the gradient coils 18 in the magnet assembly 14 to perform a series of pulse sequences, while enabling the waveform generator 28 at the proper moment during each pulse sequence to apply an oscillatory stress to the subject 10 as described in the previously-cited U.S. Pat. No. 5,592,085. The active driver 26 and the waveform generator and amplifier 28 may be housed together in a manually portable unit, denoted with a dashed line 32.

Using the above-described system, the physical properties of tissue can be measured using MR elastography (MRE) by applying the stress (e.g., tension, pressure, or shear) and observing the resulting strain (e.g., elongation, compression, rotation). By measuring the resulting strain, elastic properties of the tissue such as Young's modulus, Poisson's ratio, the shear modulus, and the bulk modulus can be calculated. By applying the stress in all three dimensions and measuring the resulting strain, the elastic properties of the tissue can be defined.

By observing the rate at which the strain decreases as a function of distance from the stress producing source, the attenuation of the strain wave can be estimated. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

Referring to FIG. 2, while an active acoustic driver such as that disclosed in the above-cited U.S. Pat. Nos. 7,034,534 and 7,307,423, can be used with the present invention, an active driver 26 includes a discrete, high-powered linear motor 34 and a rigid cylindrical housing 36 defining an acoustical chamber 37. Acoustic pressure waves are produced by the active driver 26 when the motor 34 actuates a stiffened diaphragm 38 contained within the chamber 37. The linear motor 34 converts an alternating current from the waveform generator and amplifier 28 into a reciprocating linear motion. The linear motion is translated by a drive rod 40 that extends along a motor axis 42. The drive rod 40 is attached to the diaphragm 38 located within the chamber 37.

The diaphragm 38 is comprised of a silicone rubber circular piece 44 sandwiched between two smaller diameter plastic stiffening plates 46 to form a rigid portion having a surrounding compliant perimeter 48. A portion of the compliant perimeter 48 is secured to the housing 36 between a lower chamber section 50 and an upper chamber section 52, thereby forming an air-tight seal within the chamber 37. The active driver 26 further includes a ported cap 54 to acoustically couple the tube 24 to the chamber 37.

When repeatedly stroked by the drive rod 40, the diaphragm 38 produces oscillating acoustic, or pressure, waves. This acoustic energy is transmitted via the tube 24 to the passive driver 22. The magnitude and frequency of the diaphragm 38 displacement and hence the magnitude and frequency of the pressure waves, is set by the waveform generator and amplifier 28.

The tube 24 is made of a material which is flexible, yet inelastic. The flexibility enables it to be fed along a winding path between the subject 10 in the magnet 14 and the remote site of the active driver 26. In one configuration, the tube 24 is twenty feet long and has an inner diameter of one inch. It is made of a clear vinyl material sold under the trademark TYGON and has a wall thickness of approximately one-eighth inch. TYGON is a registered trademark of Norton Company of Worchester, Mass. Alternatively, tube 24 includes a PVC tube with a reinforced wall having an inside diameter of approximately ¾ inches. The tube 24 is inelastic such that it does not expand in response to the variations in air pressure caused by the acoustic energy it conveys. As a result, the acoustic energy is efficiently conveyed from the active driver 26 to the passive driver 22.

Referring to FIGS. 7-9, passive driver 22 includes a disk-shaped back plate 200 and a circular rim 202. The back plate 200 is made of a thin, flexible, non-elastic polymer such as polycarbonate or ABS plastic, and as shown best in FIG. 9, it can bend to fit the curved contour of a subject when strapped into place over the region of interest. The strap or band may include a non-elastic material such as a fabric including a hook-and-loop fastener, or an elastic material such as neoprene. The band or strap may be disposed around the subject's body and the passive actuator is held between the subject and the strap.

An integrally molded intake pipe 204 is formed on the rim 202 of the back plate 200 and its diameter is such that the flexible tube 24 from the active driver 26 makes a tight, frictional attachment to its outer surface. The intake pipe 204 delivers the acoustic energy conveyed by the tube 24 to the space beneath the back plate 200.

An annular-shaped sealing ring 206 fastens to the bottom surface of the back plate 200 and extends downward therefrom to form the wall of an acoustic cavity indicated generally at 208 that acoustically communicates with the intake pipe 204. The sealing ring 206 is made of a closed cell foam such as that sold under the trademark "Polycell" that is injection molded in a one-step process. Polycell is a registered trademark of Imperial Chemical Industries of London, UK. The sealing ring 206 is very flexible and conforms to the contour of the subject without creating uncomfortable pressure points. The bottom edge of the sealing ring 206 engages the subject and also provides a flexible, comfortable seal around the rim 202 of the back plate 200 that confines the acoustic energy delivered by the tube 24 to the acoustic cavity 208.

To keep the back plate 200 spaced from the subject and to thereby maintain the integrity of the acoustic cavity 208 when the device is placed against and/or wrapped around a complex contoured surface, the acoustic cavity 208 is filled with an open cell foam insert 210. The insert 210 may be a solid piece of acoustically transparent material as shown, or it may be cut in a pattern. The insert 210 maintains a spacing between the subject and the back plate 200 while enabling the acoustic energy delivered through the tube 204 to be conveyed with the least possible attenuation to the subject which the insert 210 engages.

In this configuration, there is no flexible membrane fastened to the passive driver 22. Instead, a seal is made with the subject's skin around the rim 202 and the enclosed skin acts as a flexible membrane that couples the acoustic pressure waves in the cavity 208 to the tissues underneath.

Figure 10:
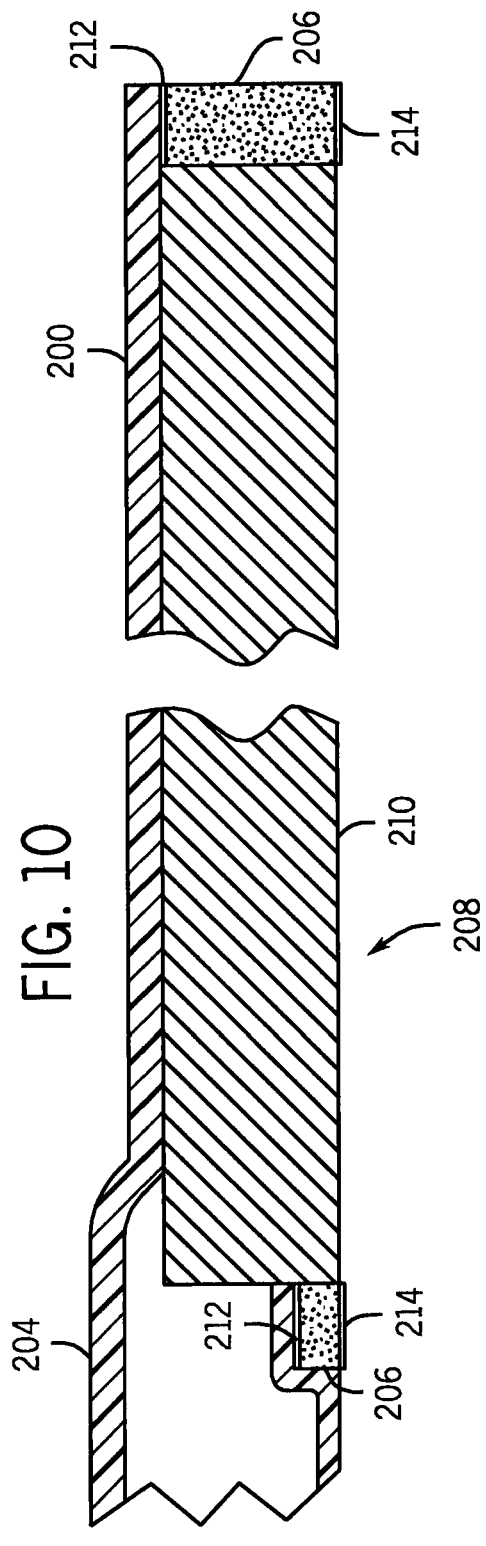
FIG. 10 is a cross-sectional view showing a first variation of the passive driver of FIG. 7.

Referring to FIG. 10, the sealing ring 206 may be attached to the rim of the back plate 200 using a layer of pressure sensitive adhesive 212. This enables the sealing ring 206 and attached foam insert 210 to be "peeled" from the back plate 200 after use and either cleaned or discarded. A new foam assembly can then be aligned with the back plate 200 and pressed into place for use with the next patient.

A less aggressive pressure sensitive adhesive 214 may also be formed on the opposite side of the sealing ring 206 that engages the subject being imaged. When the passive driver 22 is positioned on the subject to be imaged, pressure is applied around the rim of the back plate 200 to engage the pressure sensitive adhesive 214 and provide a good acoustic seal with the subject.

Figure 11:
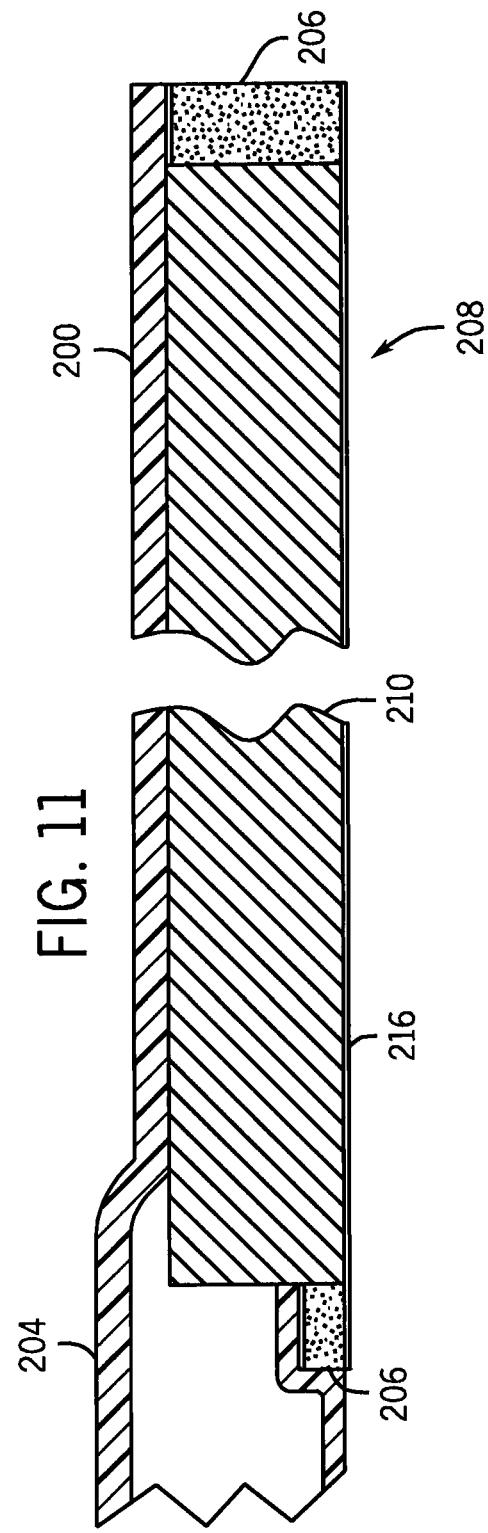
FIG. 11 is a cross-sectional view showing a second variation of the passive driver of FIG. 7.

Referring to FIG. 11, another variation is to attach a flexible membrane 216 to the bottom surface of the sealing ring 206. The membrane 216 stretches across the entire acoustic cavity 208 to seal it from the surroundings. The membrane 216 conveys the acoustic pressure waves in the acoustic cavity 208 substantially uniformly to the subject. The membrane 216 may be attached to the sealing ring with a pressure sensitive adhesive that enables it to easily be replaced after use, or the sealing ring 206, insert 210 and membrane 216 may be formed as an integral unit that can be peeled away from the back plate 200 as described above.

Referring to FIGS. 3 and 4, passive driver 22 includes a generally rectangular shaped enclosure 58 that is placed over a region of interest of a subject to be examined. The size and shape of this enclosure 58 can vary depending on the particular clinical application and the particular region of interest to be examined. The enclosure 58 is flexible so that it can be shaped to better fit the anatomical shape of the subject 10.

As shown, the enclosure 58 of the passive driver 22 is formed by a rectangular outer wall 60 and a top wall 62 joined together to define an interior chamber 56 when the enclosure 58 rests on the surface of a subject to be examined. The top wall 62 is made with a non-ferrous, non-electrically conducting flexible material such as plastic, styrofoam, cardboard, and the like. The outer wall 62 is made of a relatively compliant material including, but not limited to, closed cell foam or rubber. Both walls 60, 62 are relatively "invisible" to the magnetic fields produced in the bore 12 of the magnet 14. The end wall 60 or side wall 62 includes a hole or port 74 configured to be connected to the tube 24.

The passive driver 22 is placed against the skin 66 of the subject 10 such that the enclosure 58 and the subject 10 define a fully enclosed chamber 56. To effectuate an air-tight seal, the passive driver 22 is pressed firmly against the skin 66 and held in place with an elastic band (not shown) stretched around the subject 10. Because of the compliant nature of the materials used, the top wall 60 flexes and the outer wall 62 compresses as necessary to conform to the anatomical shape of the subject 10. A silicone gel, or similar material, may also be used to help create an airtight seal.

Standoffs 68, formed of rigid or slightly compressible material, are mounted to the top wall 60 of the enclosure 58 and extend downward a suitable depth into the chamber 56 to engage the surface of the subject 10. The standoffs 68 ensure that the surface of the subject 10 is spaced from the top wall 60 where there is substantial curvature. Although the standoffs 68 shown in FIG. 3 divide the chamber 56, the standoffs 68 may be formed in alternate shapes and arranged in a variety of placements as long as there is minimal interference with or dampening of the oscillating pressure waves.

Referring to FIG. 5, flexible passive acoustic driver 22 includes a flexible membrane 70. The passive driver 22 further includes a thin cylindrical chamber 156 defined by an end wall 160, side walls 162, and membrane 70. The end wall 160 is formed from a flexible material such as thin polycarbonate plastic, styrofoam, foam rubber, and so on. The side walls 162 are made of a flexible and relatively compliant material such as closed cell or open cell foam or rubber. The membrane 70 is made of rubber or another sufficiently elastic material. The chamber 156 is filled with a highly porous yet flexible material 72, such as a loose, woven fabric or a material such as used in a furnace or air filter.

The flexible membrane 70 is placed against the skin 66 of the subject 10 and, along with the entire passive driver 22, conforms to the shape of the subject 10. The diaphragm 70 vibrates in response to the acoustic energy received through the tube 24. The vibrations apply an oscillating stress to the skin 66 of the subject 10 which is conveyed into the region of interest as shear waves. The material 72 in the chamber 156 maintains an appropriate spacing between the skin 66 and the end wall 160 and does not impede the pressure waves traveling therethrough.

Because each of the passive drivers 22 are constructed only of materials which will not perturb magnetic fields, and further because they do not require an electric current to operate, the passive drivers 22 can be freely located anywhere within the bore 12 of the magnet 14. There is no need to align them in any particular direction to operate, and they can be placed very close to the region of interest 10 without producing image artifacts. Further, the flexible nature of the passive drivers 22 provides the ability to conform to various anatomical shapes of the subject 10.

Figure 12:
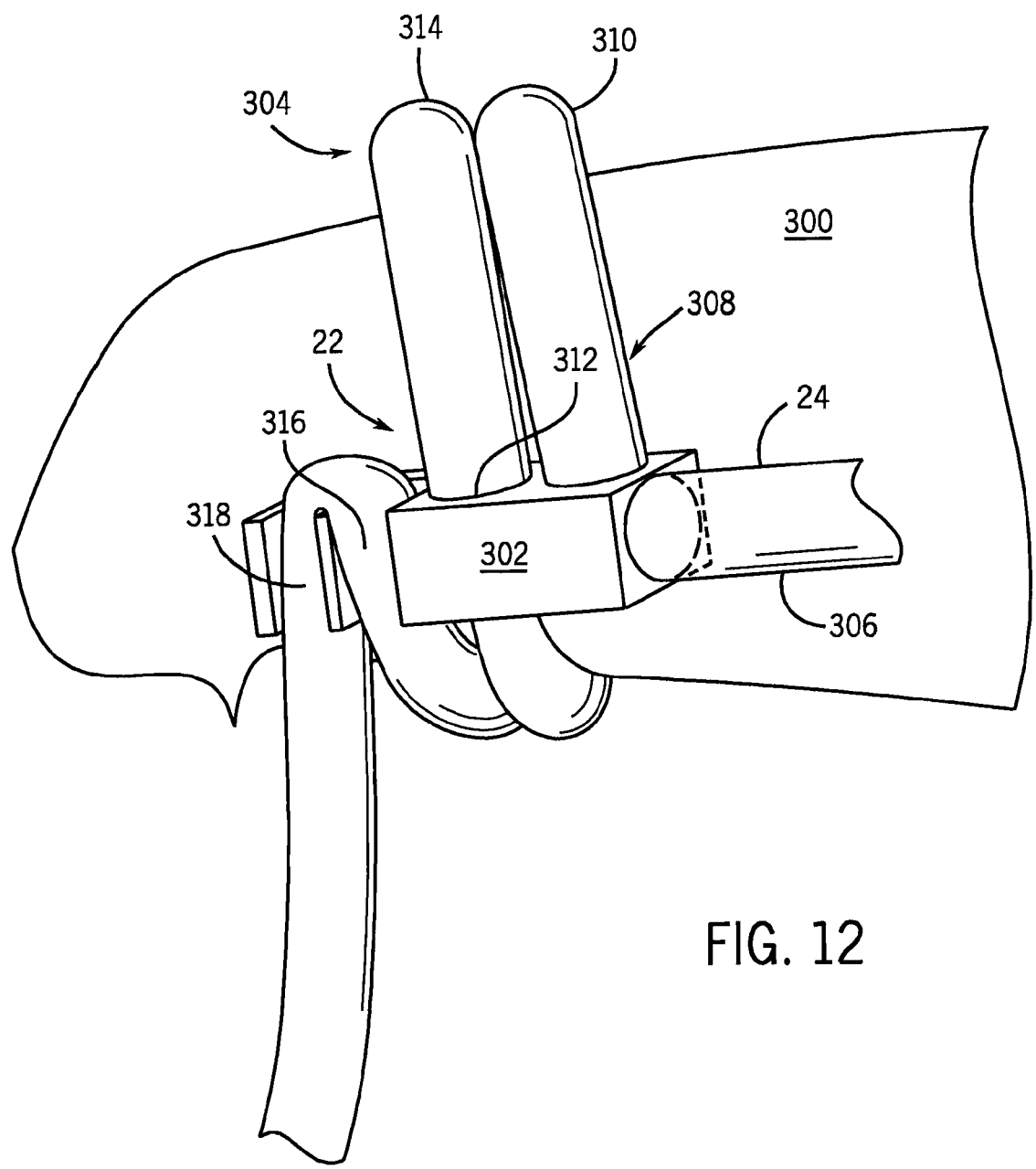
FIG. 12 illustrates a pictorial view of an alternative implementation of the passive actuator which forms part of the system of FIG. 1 and is configured to facilitate imaging of appendages.

Referring to FIG. 12, another configuration of the passive actuator 22 may be used when imaging an appendage such as an arm or leg. Passive actuator 22 is attached to the leg 300 of a patient and includes a manifold 302 which connects to tube 24 and couples the acoustic energy therein to actuator tube 304. Tube 24 connects to opening 306 at one end of manifold 302. One end of actuator tube 304 connects to output opening 308 in the top of manifold 302. Actuator tube 304 wraps around the subject's leg 300 in a first loop 310, feeds through channel 312 formed in manifold 302, and wraps around leg 300 again to form second loop 314. The distal end of actuator tube 304 wraps through two slots 316 and 318 formed in manifold 302 to pinch off the end of actuator tube 304 to form a substantially airtight seal at the end of actuator tube 304. The actuator tube 304 can be fed through the channel 312 and slots 316 and 318 to adjust the size of the loops 310 and 314 to fit snuggly around the subject's leg 300 at different locations, or to fit around the subject's arm, or other parts of the body, for example.

In this implementation, actuator tube 304 forms an air tight band around the subject's appendage and applies an oscillating constrictive force to the appendage in response to the acoustic energy delivered through the flexible tube 304 from active driver 26. Actuator tube 304 may be made of silicone tubing which expands and contracts in diameter in response to the applied acoustic energy. Expansion of the actuator tube diameter tightens or constricts around the subject's leg 300 and contraction of the diameter loosens the grip around the leg 300. This oscillating constrictive force applied around an appendage has been found to produce good MRE images of structures in the appendage.

Depending upon the system configuration, actuator tube 304 may be formed in any number of turns around the subject's appendage. In some cases, a single turn may be sufficient to transfer acoustic energy from actuator tube 304 into the subject's appendage for medical imaging. Other implementations, however, call for many turns formed around the appendage to ensure sufficient delivery of acoustic energy from passive driver 22 into appendage 300.

Although the implementation of passive driver 22 illustrated in FIG. 12 provides utility in its being able to conform around the body surface in a plurality of configurations, the configuration of actuator tube 304 can greatly affect the efficiency with which actuator tube 304 and passive driver 22 transmit acoustic energy into appendage 300 of the subject.

Figure 13A:
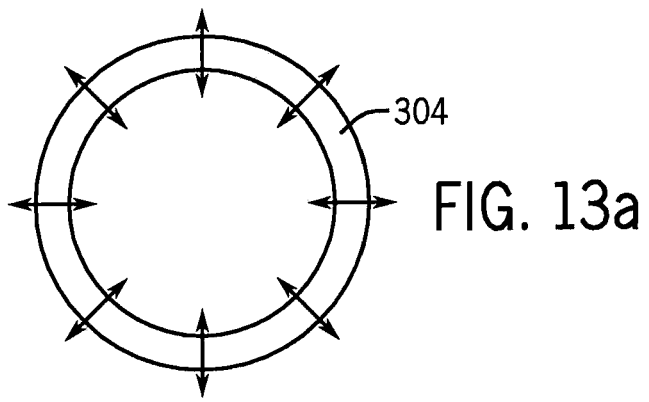
FIGS. 13a-13d illustrate cross-sectional views of various tube configurations of the passive driver illustrated in FIG. 12.

FIG. 13a illustrates a cross-sectional view of actuator tube 304 having a wall of consistent thickness. As the internal pressure of actuator tube 304 varies due to the pressure variations driven by active acoustic driver 26, actuator tube 304 expands and contracts equally in all directions (as illustrated by the double-headed arrows on FIG. 13a). Even though the circumference of actuator tube 304 vibrates equally in all directions, only the portions of actuator tube 304 that contact appendage 300 transfer energy into appendage 300. The other portions of actuator tube 304 that vibrate in the open air do not transfer energy. Thus, those vibrations are wasted energy. As such, only a limited amount of the acoustic energy transmitted to actuator tube 304 by active acoustic driver 26 is transmitted to the subject.

The configuration of actuator tube 304 depicted in FIG. 13a may also negatively affect the fidelity of the mechanical vibrations transferred into appendage 300 by passive driver 22 resulting in inaccurate, or noisy images. Because actuator tube 304 of FIG. 13a generates mechanical vibrations equally in all directions, each winding of actuator tube 304 can communicate mechanical vibration (and noise) into nearby turns of actuator tube 304. In an actuator tube 304 with multiple windings, for example, the vibrations of a first winding of actuator tube 304 may interfere with other, proximate windings. With reference to FIG. 12, because a portion of actuator tube 304 making up loop 310 vibrates in a horizontal direction, the walls of loop 310 may contact actuator tube 304 making up loop 314 transferring mechanical vibrations thereto. As such, interference may be introduced into the system due to the multiple loops in actuator tube 304 transmitting destructive or out-of-sync acoustic waves into other one another.

Figure 13B:
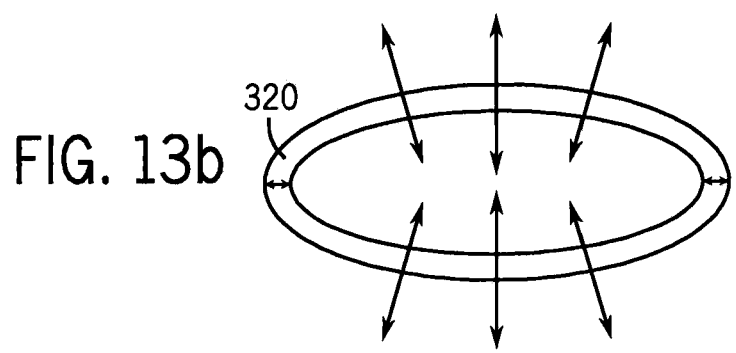

FIG. 13b illustrates a cross-sectional view of actuator tube 320 that is configured to increase the efficiency of energy transfer between passive driver 22 and subject 300. Actuator tube 320 has a flattened, oval cross-section and may include elastic or inelastic materials. At the narrowest portion of the cross-section, the oval shape of actuator tube 320 may included rounded or sharp corners. As pressure fluctuations are generated within actuator tube 320, there is more expansion or vibration along the flattened portions of actuator tube 320 than at the narrow edges of actuator tube 320 (as illustrated by the double-headed arrows). As a result, the mechanical vibration of actuator tube 320 occurs primarily in an up-down orientation, increasing the amount of energy delivered to subject 300, while minimizing lost energy and energy communicated between loops of actuator tube 320. Furthermore, the expansion and contraction that results in actuator tube 320 is more efficient. Because the intraluminal pressure is greater in actuator tube 320 than actuator tube 304, the vibrations in actuator tube 320 only require bending of the tube wall, rather than circumferential stretching of the tube wall. In short, the walls of actuator tube 320 only have to flex to deliver vibrational energy to subject 300, an action that requires less energy than stretching and provides greater efficiency. Actuator tube 320 may ultimately be fabricated with a relatively inelastic material such as vinyl. Other materials which do not stretch, but bend easily may also be used to fabricate actuator tube 320.

Figure 13C:
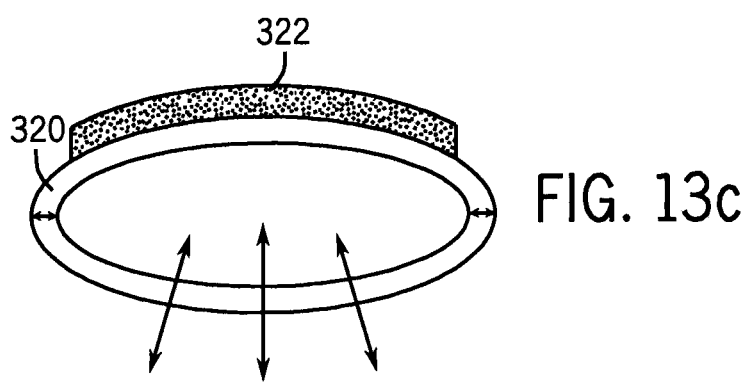

FIG. 13c illustrates a configuration of actuator tube 320 wherein an inelastic strap 322 is formed around the free flat face of actuator tube 320. Strap 322 prevents outward motion of actuator tube 320 at the outer surface (away from appendage 300, for example) to improve the transfer of vibrational energy from actuator tube 320 into subject 300.

Figure 13D:
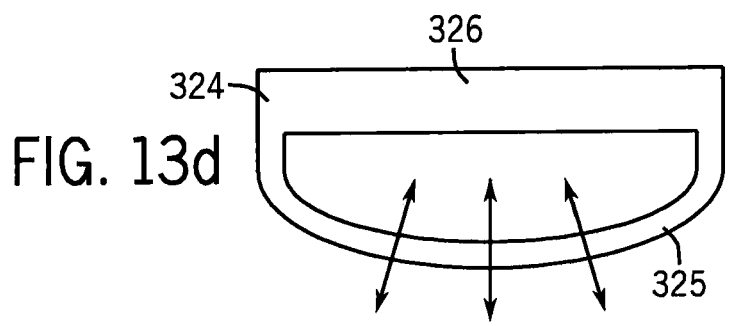

FIG. 13d illustrates alternative actuator tube 324 having a single rigid surface 326 disposed opposite flexible face 328. Actuator tube 324 may be fabricated using an extrusion method wherein one side of the actuator tube is flexible, while another side is rigid. Alternatively, both sides of actuator tube 324 are flexible, while only one side of the tube has elasticity. By positioning the flexible face of actuator tube 324 against subject 300, the amount of vibration energy delivered to subject 300 is maximized, as illustrated by the double-headed arrows.

In some situations, MRE may be used to monitor the tissue at a location where cannulas, or other medical instruments are present within body tissue of a subject. For example, MRE may be used to monitor the ablation of tissue at the tip of a laser ablation cannula. When using a cannula, acoustic energy can be delivered into the subject by applying a vibrational energy along the axis of the cannula. The energy is then transferred from the cannula into the surrounding tissue in an ideal cylindrically symmetrical shear wave field to facilitate MRE.

A drum-like driver may be used to deliver the vibrational energy into the cannula. A fitting is placed on the diaphragm of the passive driver allowing the driver to be connected to or fixed to the cannula. The driver is then anchored either to the body wall or a stationary object, so that forces generated at the diaphragm of the driver can be transferred to the cannula. In this example implementation, however, motions of the body wall such as breathing or other patient motion relative to the static anchor point on the passive driver could move the tip of the cannula inside the body away from the selected location, negatively affecting the fidelity and accuracy of any MRE.

It is possible to generate inertial effects within the passive driver by incorporating a weight into the passive driver. For example, if a drum-like driver is used within the system, a weight, possibly including a heavy material such as lead, or ceramic, may be bonded to the diaphragm. Generally, the weight includes a non-ferrous material as to be compatible with the operation of the MIR system. The weight may also include non-electrically conductive materials to reduce the possibility of image artifacts. To protect the excursions of the diaphragm of the driver during operation, the diaphragm may be protected by enclosing it within the driver unit.

Figure 14:
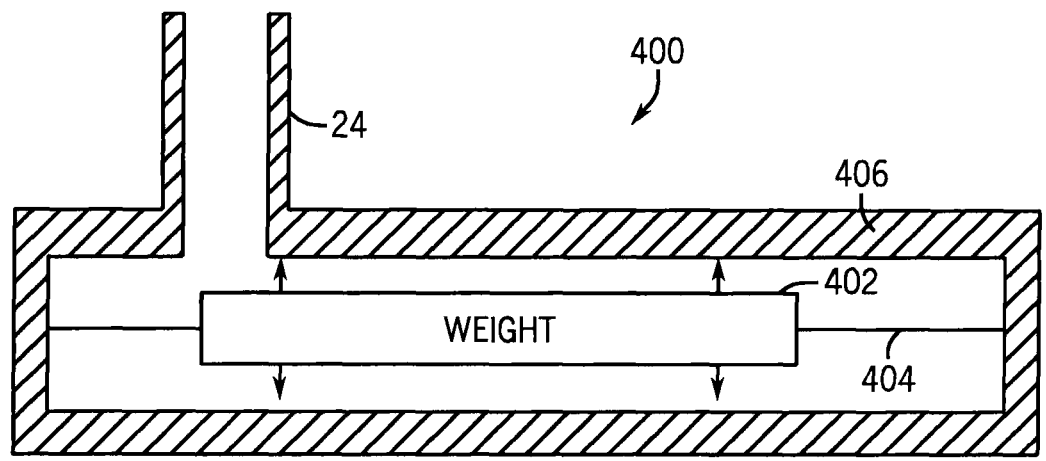
FIG. 14 illustrates a cross-sectional view of an inertial driver incorporating a weight mounted to a diaphragm of the driver.

FIG. 14 illustrates inertial passive driver 400 incorporating a weight mounted to a diaphragm of the driver. Inertial driver 400 includes weight 402 mounted to diaphragm 404. Weight 402 may be mounted to diaphragm 404 using adhesive, or any other attachment mechanism. For example, weight 402 may be removably mounted to diaphragm 404 to allow different weights for different applications to be used within the same inertial driver 400. Alternatively, weight 402 is integrated into diaphragm 404 during the fabrication process of diaphragm 404, for example by integrating a heavier material into a central region of diaphragm 404, or substantially altering the geometry of diaphragm 404 material near the central region. Both weight 402 and diaphragm 404 are mounted within enclosure 406 which protects diaphragm 402. Tube 24 is mounted to inertial driver 400 to communicate acoustic energy into inertial driver 400 to vibrate diaphragm 404 and weight 402. During the operation of inertial driver 400, diaphragm 402 and weight 402 vibrate as indicated by the double-headed arrows of FIG. 14. The vibrations are communicated to enclosure 406, which may then be communicated into a cannula or other medical instrument for MRE.

Unlike other passive driver configurations, where acoustic or vibrational energy is delivered only on the face of the diaphragm, inertial driver 400 delivers acoustic energy on any external surface of the device (which could be flat or curved) including enclosure 406. As such, inertial driver 400 does not need to be anchored during operation.

Figure 15:
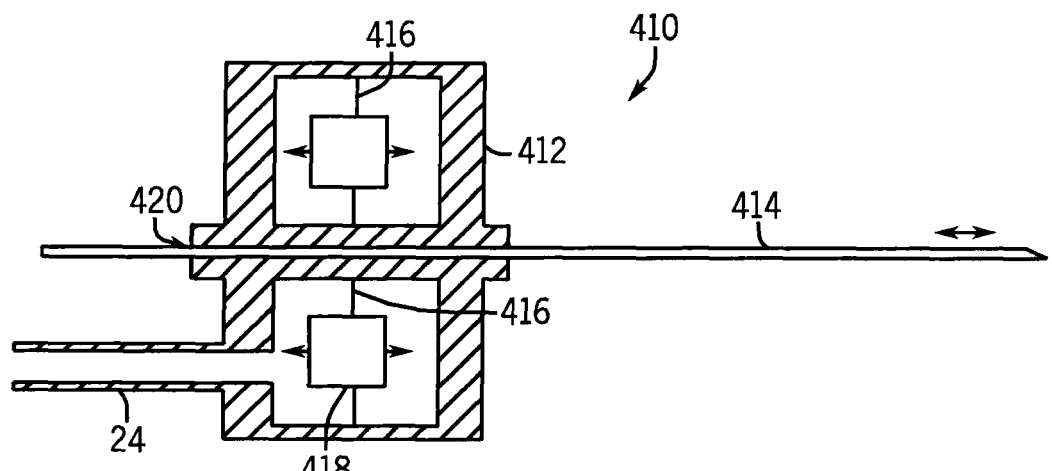
FIG. 15 illustrates a cross-sectional view of an inertial driver providing inertial effects and being configured to slide co-axially over a cannula.

FIG. 15 illustrates a cross-section view of inertial driver 410 providing inertial effects and being configured to slide co-axially over a cannula, or other medical instrument. Inertial driver 410 includes enclosure 412 for protecting the device. Enclosure 412 is configured to mount to and communicate vibrations into cannula 414. Diaphragm 416 is mounted within enclosure 412, and weight 418 is mounted to diaphragm 416. Tube 24 is mounted to inertial driver 410 to communicate acoustic energy into inertial driver 410 to vibrate diaphragm 416 and weight 418. During operation of inertial driver 410, diaphragm 416 and weight 418 vibrate as indicated by the double-headed arrows of FIG. 15.

In FIG. 15, enclosure 412, weight 418 and diaphragm 416 are toroid-shaped (for example, ring or donut-shaped) and fit around cannula 414. Enclosure 412, weight 418 and diaphragm 416 include central port 420 configured to receive cannula 414. Once mounted, a portion of the inner wall of port 420 may contact an outer surface of cannula 414. By sliding cannula 414 through port 420, inertial driver 410 can be positioned at various locations along the length of cannula 414.

As inertial driver 410 operates, inertial driver 410 delivers vibrational energy along the axis of cannula 414 (illustrated by the double-headed arrows on FIG. 15). In this configuration, vibrational energy is delivered to cannula 414, or any other medical instrument to which inertial driver 410 is mounted, without the need to mount the driver to a fixed anchor point. As such, any movements of the subject that occur during MRE have negligible affect on the vibrations delivered to the internal tissues of the subject.

Using passive driver 410 of FIG. 15, vibrational energy is communicated to the internal tissues of the subject to facilitate the monitoring of the tissues using MRE. In one specific application, passive driver 410 is mounted to an endorectal cannula to deliver acoustic energy in the form of vibrational energy, allowing shear waves to be delivered for prostate imaging with MRE. The present system is not interrupted by movements of the subject, as it provides for coupling passive driver 410 directly to cannula 414.

Thus, the present system provides a mechanism for introducing vibrations into abdominal organs, or other body parts of a subject for performing MR elastography or other medical imaging. Specifically, a passive driver is described. The passive driver is configured to communicate vibrational energy generated by an active driver into a subject. For example, a driver may be configured to be placed against the thorax of the subject above, for example, the ribcage to induce a vibration against a wall of the subject's body. The vibration is communicated to the subject's ribcage, which operates as an extension of the passive driver creating cyclic pressure variations across the diaphragm, between, for example, the thorax and abdomen. Shear waves are generated in the abdomen via mode conversion at multiple locations, particularly where the diaphragm contacts upper abdominal organs and at retroperitoneal locations. The system may operate to eliminate unexpected preload to the abdominal organs, further enhancing the reliability of shear stiffness measurements with MRE.

In addition, the system may provide for increased variations in the strength of the transdiaphragmatic pressure by placing a second passive driver, driven 180 degrees out of phase, against the abdominal wall. In this case, a strap mechanism is placed around the subject to secure the driver to the subject. Using the strap, one or more drivers may be secured to the subject's body at various positions to optimize the location of the drivers depending upon the application. For example, when imaging the kidneys, the strap may be used to position one or more passive drivers to provide optimal energy transfer from the drivers to the kidneys to improve imaging resolution. The system may be used in combination with MR or ultrasound medical imaging.

The present invention produces and delivers stress levels that are much larger than those produced by prior art drivers, even other passive acoustic drivers. Unlike the prior art passive drivers which have a rigid housing a diaphragm mounted thereon, the embodiments of the present invention closely and comfortably couples to the subject for consistent driver efficiency and imaging.

The invention claimed is:

1. An acoustic driver system for producing a stress on a subject undergoing an imaging procedure, comprising:
    an active driver located remotely from the subject and configured to generate oscillating acoustic energy; and
    a passive driver, the passive driver including:
    an enclosure configured to mount to a medical instrument, the medical instrument being configured to be inserted into a tissue of the subject;
    a diaphragm disposed within the enclosure, the diaphragm being configured to vibrate within the enclosure, and
    a weight mounted to the diaphragm, the weight being configured to move with the diaphragm;
    wherein the active driver is acoustically coupled to the passive driver such that the diaphragm of the passive driver and the medical instrument vibrate in response to the acoustic energy produced by the active driver.

2. The acoustic driver system of claim 1, wherein the weight is mounted to a central region of the diaphragm.

3. The acoustic driver system of claim 1, wherein the weight includes a lead or a ceramic material.

4. The acoustic driver system of claim 1, wherein the medical instrument includes a cannula.

5. The acoustic driver system of claim 4, wherein the cannula includes an endorectal cannula, and the passive driver is configured to deliver vibrational energy to a prostate of the subject.

6. The acoustic driver system of claim 4, wherein the cannula is configured to perform tumor ablation.

7. The acoustic driver system of claim 1, wherein the passive driver is configured to slide along a length of the medical instrument.

8. The acoustic driver system of claim 1, wherein the enclosure includes a port formed through a central region of the passive driver, a surface of the port being configured to contact a surface of the medical instrument.

9. The acoustic driver system of claim 8, wherein the enclosure is substantially toroidal.

\* \* \* \* \*